United States Patent
Komatsu et al.

(10) Patent No.: US 9,267,902 B2
(45) Date of Patent: Feb. 23, 2016

(54) METHOD OF ANALYZING SAMPLE USING SECONDARY ION EMITTED FROM SAMPLE AND ANALYZER FOR PERFORMING ANALYSIS METHOD

(75) Inventors: Manabu Komatsu, Kawasaki (JP);
Masafumi Kyogaku, Yokohama (JP);
Hiroyuki Hashimoto, Yokohama (JP);
Naofumi Aoki, Nagoya (JP)

(73) Assignee: Canon Kabushiki Kaisha, Tokyo (JP)

(*) Notice: Subject to any disclaimer, the term of this patent is extended or adjusted under 35 U.S.C. 154(b) by 28 days.

(21) Appl. No.: 13/979,144

(22) PCT Filed: Jan. 12, 2012

(86) PCT No.: PCT/JP2012/051011
§ 371 (c)(1),
(2), (4) Date: Aug. 8, 2013

(87) PCT Pub. No.: WO2012/096412
PCT Pub. Date: Jul. 19, 2012

(65) Prior Publication Data
US 2013/0320204 A1    Dec. 5, 2013

(30) Foreign Application Priority Data

Jan. 14, 2011 (JP) ................................ 2011-006094
Nov. 17, 2011 (JP) ................................ 2011-251621

(51) Int. Cl.
*H01J 49/00*      (2006.01)
*G01N 23/22*      (2006.01)
(Continued)

(52) U.S. Cl.
CPC ........ *G01N 23/2202* (2013.01); *H01J 49/0468* (2013.01); *H01J 49/142* (2013.01)

(58) Field of Classification Search
CPC ... H01J 49/00; H01J 49/0004; H01J 49/0013; H01J 49/0022; H01J 49/0027; H01J 49/0045; H01J 49/0054; H01J 49/0068; H01J 49/0077; H01J 49/0095; H01J 49/0459; H01J 49/0463; H01J 49/0468; H01J 49/0472; H01J 49/164

USPC ........... 250/281, 282, 288, 289, 492.1, 492.2, 250/492.21, 492.3
See application file for complete search history.

(56) References Cited

U.S. PATENT DOCUMENTS 4,740,697 A *   4/1988   Suzuki ............................ 850/11
5,507,154 A *   4/1996   Grant .............................. 62/156
(Continued)

FOREIGN PATENT DOCUMENTS

JP          8-273585 A     10/1996

OTHER PUBLICATIONS

Conlan et al., Is proton cationization promoted by polyatomic primary ion bombardment during time-of-flight secondary ion mass spectrometry analysis of frozen aqueous solutions?, Mar. 23, 3006, Rapid Communications in Mass Spectrometry, vol. 20, Issue 8, pp. 1327-1334.*

Roddy et al., Proton Transfer in Time-of-Flight Secondary Ion Mass Spectrometry Studies of Frozen-Hydrated Dipalmitoylphosphatidylcholine, Anal. Chem. 2003, 75, pp. 4087-4094.*

(Continued)

*Primary Examiner* — Michael Logie
*Assistant Examiner* — Jason McCormack
(74) *Attorney, Agent, or Firm* — Fitzpatrick, Cella, Harper & Scinto

(57) ABSTRACT

Provided is a sample analysis method of irradiating a sample with a primary ion beam to analyze a secondary ion emitted from the sample by mass spectrometry, the sample analysis method including the steps of cooling a sample placed in a chamber; forming an ice layer on a surface of the cooled sample by discharging one of water and an aqueous solution to the chamber; and irradiating the surface of the sample with the primary ion beam with the ice layer being formed thereon, wherein an amount of the water forming the ice layer is 0.1 $ng/mm^2$ or more and 20 $ng/mm^2$ or less.

20 Claims, 8 Drawing Sheets

(51) Int. Cl.
*H01J 49/04* (2006.01)
*H01J 49/14* (2006.01)

(56) References Cited

U.S. PATENT DOCUMENTS

| | | | |
|---|---|---|---|
| 5,643,800 A * | 7/1997 | Tarantino et al. | 436/518 |
| 6,825,045 B2 * | 11/2004 | Haglund et al. | 436/174 |
| 7,446,309 B2 | 11/2008 | Murayama et al. | |
| 2006/0118711 A1 | 6/2006 | Murayama et al. | |
| 2008/0054176 A1 * | 3/2008 | Hiraoka | 250/288 |
| 2008/0124903 A1 * | 5/2008 | England et al. | 438/530 |
| 2008/0203286 A1 * | 8/2008 | Loboda | 250/281 |
| 2010/0136255 A1 * | 6/2010 | Notte, IV | C23C 14/06 427/534 |
| 2010/0155591 A1 * | 6/2010 | Matsuo | 250/282 |
| 2010/0181500 A1 * | 7/2010 | Chang et al. | 250/492.21 |
| 2011/0248156 A1 * | 10/2011 | Komatsu et al. | 250/251 |
| 2013/0037707 A1 * | 2/2013 | Lamberti et al. | 250/282 |

OTHER PUBLICATIONS

Xavier A. Conlan et al., "Is Proton Cationization Promoted by Polyatomic Primary Ion Bombardment During Time-of-Flight Secondary Ion Mass Spectrometry Analysis of Frozen Aqueous Solutions?" 20 Rapid Commun. Mass Spectrom. 1327-1334 (Mar. 2006).

Manabu Komatsu et al., "Enhanced Peptide Molecular Ion Imaging with Time-of-Flight Secondary Ion Mass Spectrometry and Its Application with Ink-Jet Printing Technology for Bio-Material Analysis," 14(3) Journal of Surface Analysis 187-195 (2008).

Thomas P. Roddy et al., "Proton Transfer in Time-of-Flight Secondary Ion Mass Spectrometry Studies of Frozen-Hydrated Dipalmitoylphosphatidylcholine," 75(16) Anal. Chem. 4087-4094 (Jul. 2003).

Paul D. Piehowski et al., "Freeze-Etching and Vapor Matrix Deposition for ToF-SIMS Imaging of Single Cells," 24 (15) Langmuir 7906-7911 (Jun. 2008).

* cited by examiner

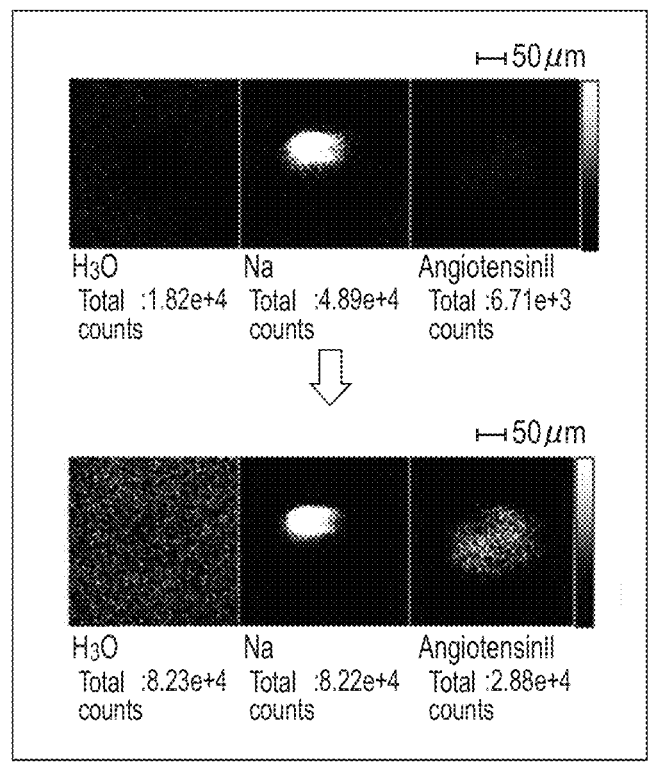
FIG. 5A
FIG. 5B
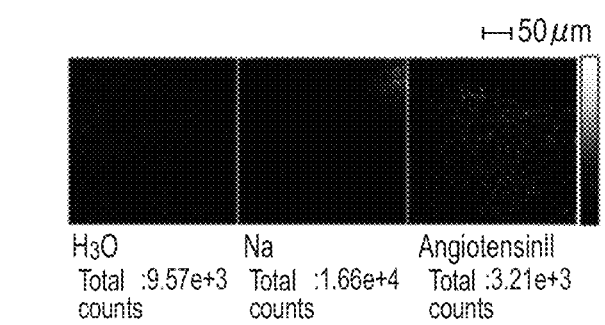
FIG. 5C
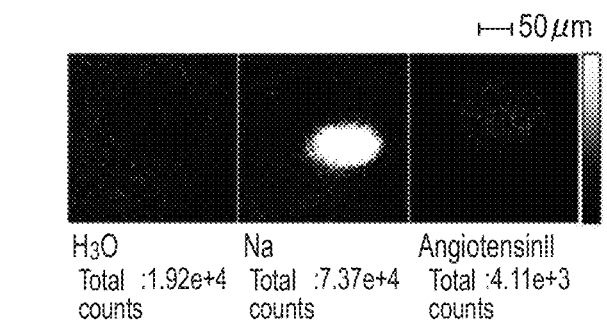
FIG. 5D

METHOD OF ANALYZING SAMPLE USING SECONDARY ION EMITTED FROM SAMPLE AND ANALYZER FOR PERFORMING ANALYSIS METHOD

TECHNICAL FIELD

The present invention relates to a sample analysis method including a step of desorbing and ionizing a sample constituent by using a primary beam selected from ions, neutral particles, electrons, and laser light as well as to an analyzer therefor.

BACKGROUND ART

There is known an analysis method of thoroughly visualizing the expression amount of a protein expressed in a tumor tissue or the like based on a mass signal intensity by using a Matrix Assisted Laser Desorption/Ionization (MALDI) or a Time of Flight-Secondary Ion Mass Spectroscopy (TOF-SIMS).

In the measurement of a biological sample by the MALDI or TOF-SIMS, a sample constituent is detected in an ionized state. In particular, the sample constituent is detected as a protonated molecule in most cases.

In the measurement of a biological sample by the MALDI or TOF-SIMS, in order to enhance the ionization efficiency of a constituent, a method of supplying an aqueous solution of a matrix, an alkali metal salt, or an acidic substance to a sample by spraying or dropping has been performed. For example, the inventors of the present invention found that the ionization efficiency of a sample is enhanced in the TOF-SIMS measurement by dropping an acidic substance aqueous solution to the sample (PTL 1).

On the other hand, there is also known a method of promoting protonation to a sample constituent by using water contained in the sample or by providing water to the sample from outside, instead of using a matrix or an acidic substance.

NPL 1 discloses a method of measuring a fracture cross-section of sample suspensions which are prepared by sonicating and freezing in H2O.

NPL 2 discloses a method of allowing a sample to adsorb water by freezing the sample in a water atmosphere to generate a protonated molecule.

CITATION LIST

Patent Literature

PTL 1: U.S. Pat. No. 7,446,309

Non Patent Literature

NPL 1: Analytical Chemistry 2003, 75, P4087
NPL 2: Langmuir 2008, 24, P. 7906

SUMMARY OF INVENTION

Technical Problems

According to the method of enhancing an ion detection efficiency by providing an aqueous solution to a sample by dropping, a water-soluble sample constituent may flow into liquid droplets in some cases. Therefore, the original information on a distribution of the sample constituent cannot be obtained.

Further, according to the methods of NPLs 1 and 2, there is a problem in that the ion detection sensitivity is reduced due to a great amount of ice covering the surface of a sample.

It is therefore an object of the present invention to provide a sample analysis method and analyzer capable of detecting a sample constituent with good sensitivity while keeping the original information on a distribution of the sample constituent.

Solution to Problems

In order to solve the above-mentioned problems, the present invention provides a sample analysis method of irradiating a sample with a primary ion beam to analyze a secondary ion emitted from the sample by mass spectrometry, the sample analysis method including: cooling a sample placed in a chamber; forming an ice layer on a surface of the cooled sample by discharging one of water and an aqueous solution to the chamber; and irradiating the surface of the sample with the primary ion beam with the ice layer being formed thereon, in which an amount of the water forming the ice layer is 0.1 ng/mm$^2$ or more and 20 ng/mm$^2$ or less.

Further, in order to solve the above-mentioned problems, the present invention provides an analyzer of irradiating a sample with a primary beam to analyze an ion emitted from the sample, the analyzer including: a chamber in which the sample is to be placed; a primary beam generating unit for irradiating a surface of the sample in the chamber with the primary beam; a cooling mechanism for cooling the sample in the chamber; a discharge unit for discharging one of water and an aqueous solution to the chamber; an extraction electrode for guiding a secondary ion emitted from the sample to a mass analysis unit; and a control unit for controlling an amount of the one of the water and the aqueous solution to be discharged from the discharge unit to the chamber, in which one of the water and the aqueous solution is discharged from the discharge unit with the sample placed in the chamber being cooled to form an ice layer on the surface of the sample.

Advantageous Effects of Invention

According to the present invention, a high ionization promoting effect can be obtained with the suppressed outflow of a water-soluble component constituting an object, by providing a prescribed amount of ice to the surface of a sample. Thus, it is possible to provide the method and analyzer capable of detecting a sample constituent with good sensitivity while keeping the original information on a distribution of the sample constituent.

BRIEF DESCRIPTION OF DRAWINGS

FIGS. 5A, 5B, 5C and 5D show TOF-SIMS ion images obtained in Example 1 and Comparative Examples 1-5 and 1-6.

DESCRIPTION OF EMBODIMENTS

Configuration of an Analyzer

Figure 1:
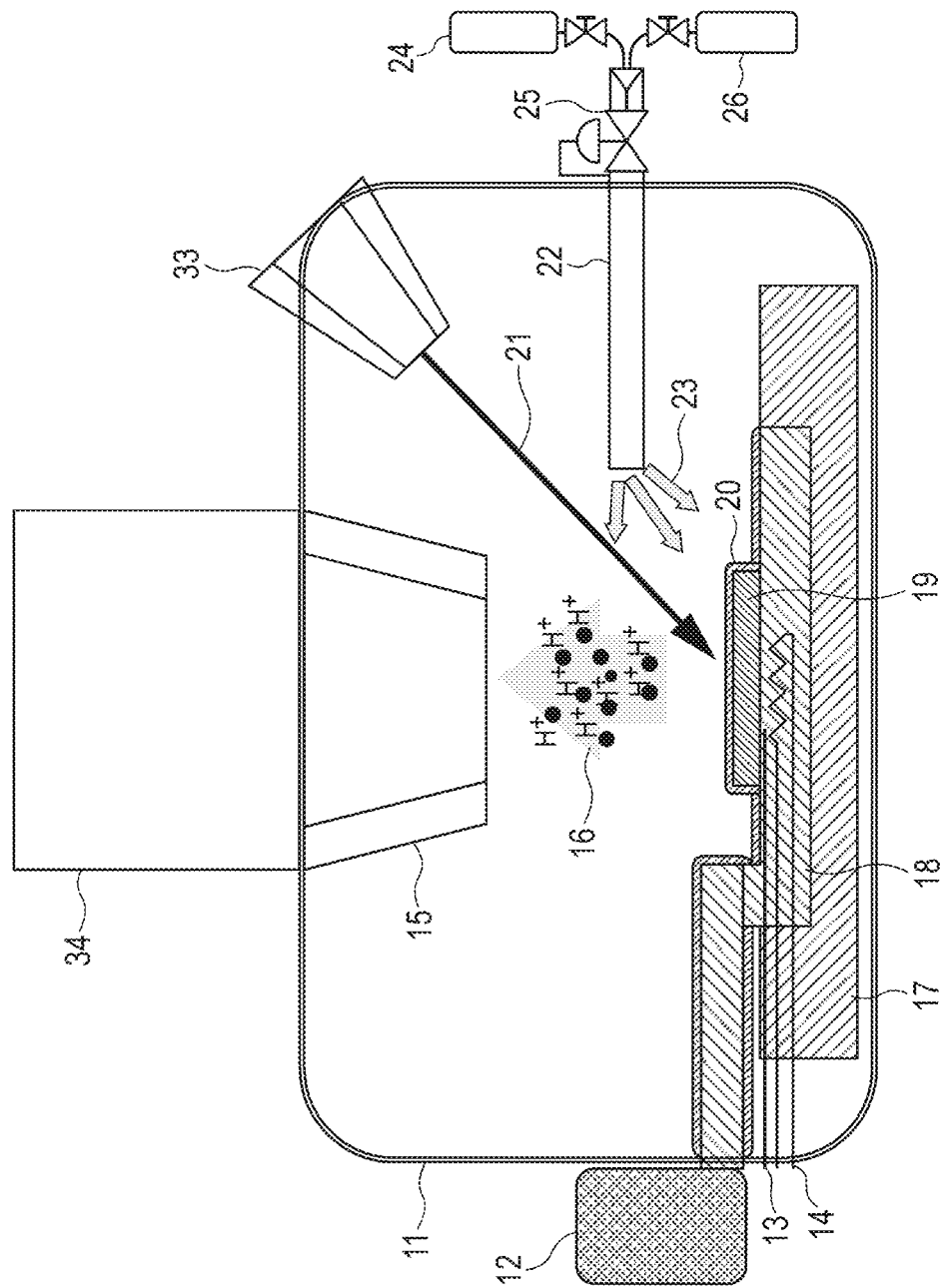
FIG. 1 is a view illustrating an example of an analyzer of the present invention.

FIG. 1 illustrates an example of an analyzer of this embodiment. As illustrated in FIG. 1, the analyzer includes a primary beam generating unit 33 that generates a primary beam selected from ions, neutral particles, electrons, and laser light. In the analyzer, a sample 19 is irradiated with the primary beam generated from the primary beam generating unit 33, and ions emitted from the sample can be analyzed. By changing the irradiation position, secondary ions are emitted from the sample at the irradiation position, and mass information is obtained by using a mass analysis unit 34 connected to an upper part of an extraction electrode 15. Based on the mass information thus obtained, information on a distribution of a constituent constituting the sample 19 is obtained.

An object refers to anything that can be measured by mass spectrometry. Examples of the object include a polymer compound, a low-molecular compound, an organic compound, an inorganic compound, a biological object, an organ, a sample derived from a biological object, a tissue segment, a cell, and a cultured cell. Examples of the component constituting the object include an organic compound, an inorganic compound, a protein, a peptide, a sugar chain, a polynucleotide, and an oligonucleotide.

As the mass spectrometry, any mass spectrometry can be used. Above all, there is used a mass spectrometry, which adopts MALDI, SIMS, or Fast Atom Bombardment (FAB) as an ionization method and adopts a time-of-flight, magnetic field deflecting, quadrupole, ion trap, or Fourier transform ion cyclotron resonance type as an analysis portion. Any one of these mass analysis units is arranged in an upper part of the extraction electrode 15 of FIG. 1.

According to the above-mentioned mass spectrometry, information on mass is obtained as a signal intensity in a value obtained by dividing a mass by a charge (mass-to-charge ratio m/z). As illustrated in FIG. 1, the analyzer of the present invention includes the primary beam generating unit 33 for irradiating a sample with a primary beam 21, and a mechanism for accelerating ions 16 desorbed from the sample in the extraction electrode 15 to draw the ions 16 into the mass analysis unit, thereby performing the above-mentioned mass analysis. As the primary beam, an ion beam is preferred.

As illustrated in FIG. 1, the analyzer of the present invention includes, below the sample 19, a sample cooling mechanism (cooling portion) 18 capable of cooling a sample by thermal contact with a liquid nitrogen tank 12 placed outside of a measurement chamber 11, a heating wire heater (heating portion) 14 for heating, and a thermocouple 13 for monitoring temperature. The temperature regulating mechanism can keep the sample at a predetermined temperature in a range of 40° C. to −160° C.

Further, the analyzer of this embodiment also includes a discharge unit 22 for discharging water or an aqueous solution into a chamber, and a control unit 25 for controlling the amount of water or an aqueous solution to be discharged into the chamber.

In this embodiment, the discharge unit is arranged as a gas leaking nozzle 22 that discharges a gas 23 containing a solution component. The gas leaking nozzle 22 is connected to a solution tank 24 and a carrier gas cylinder 26 mounted to the outside of the measurement chamber 11 through a gas-liquid mixing valve 25. By changing the gas-liquid mixing ratio, the concentration of a solution contained in gas to be discharged, that is, the amount of water or an aqueous solution to be discharged to the chamber can be regulated. At this time, in order to suppress the contamination in the chamber and the burden on the vacuum system, it is desired that the discharge port of the gas leaking nozzle 22 be installed as close to the surface of the sample as possible.

Here, only water may be used as a solution to be discharged in a gaseous form, but an aqueous solution containing, as a solute component, any one of a matrix, an alkali metal salt, and an acidic substance having the effect of enhancing an ionization efficiency may be used. Examples of the matrix include α-cyano-4-hydroxycinnamic acid (CHCA), 2,5-dihydroxybenzoic acid (DHBA), and sinapinic acid (SA). Examples of the alkali metal salt include sodium carbonate, potassium carbonate, sodium chloride, and potassium chloride. Examples of the acidic substance include acetic acid, trifluoroacetic acid, and perfluorosuberic acid. Further, examples of the carrier gas include inactive gas such as nitrogen gas and argon gas.

Sample Analysis Method

Hereinafter, a method of analyzing a sample by using the analyzer of FIG. 1 is described.

As illustrated in FIG. 1, a sample placed in the measurement chamber 11 is cooled. In order to prevent water in the chamber from being attached to the sample during cooling, the sample may be cooled under the condition of a reduced pressure. At this time, the pressure may be set to be $10 \times 10^{-6}$ Pa or less, preferably $3 \times 10^{-6}$ Pa or less.

Then, water or an aqueous solution is discharged into the chamber to form an ice layer on the surface of the cooled sample. As described below, in the step of forming the ice layer, the amount of ice to be formed on the surface of the sample can be controlled with good precision by discharging water or an aqueous solution in a controlled discharge amount to the chamber. After that, the surface of the sample is irradiated with a primary beam with the ice layer formed on the sample, with the result that ions (secondary ions) are emitted from the sample. The emitted secondary ions are guided to the mass analysis unit 34 through the extraction electrode 15, and thus, mass analysis can be performed.

The inventors of the present invention paid attention to the ice layer to be formed on the surface of the sample and earnestly conducted studies thereon.

As a result, the inventors have found that, by setting the amount of water to be 0.1 ng/mm² or more and 20 ng/mm² or less in the ice layer to be formed on the surface of the sample which is to be irradiated with the primary ion beam, ion detection sensitivity is high, and the original information on a distribution of the sample constituent can be kept, and thus, achieved the invention of the present application.

Step of Forming an Ice Layer

The inside of the measurement chamber 11 is vacuumized. Then, the gas-liquid mixing valve 25 is opened to cause a gas containing a solution component to be discharged from the tip end of the gas leaking nozzle 22. At this time, by previously cooling the sample 19 to a temperature equal to or lower than a freezing point or a sublimation point of the solution, the solution component adsorbs to the surface of the sample 19 in an ice form to form ice 20. At this time, by regulating the concentration of the solution component contained in the gas to be discharged, the gas discharge amount, the exposure time to a gas atmosphere of the sample, and the sample temperature, the attached amount of the ice 20 to be formed on the surface of the sample can be regulated.

As another method of forming ice, a solution may be sprayed onto the surface of the sample in a liquid form by an electrospray method or an electron spray method. At this time, the chamber 11 may be filled with inactive gas under a certain pressure before the solution is sprayed onto the surface of the sample. It is necessary to minutely regulate parameters such as the shape of the tip end of a spray nozzle, the spray speed of a spray, the spray amount, the distance to the surface of the sample, and the kind and pressure of inactive gas so that the solution adsorbs to the surface of the sample in a uniform amount while forming as small liquid droplets as possible. In the same way as in the above, by previously cooling the sample 19 to a temperature equal to or lower than the freezing point or sublimation point of the solution, the solution component is attached to the surface of the sample 19 in an ice form.

The ice to be formed on the surface of the sample can have a discretely distributed form or a continuous filmy form. The discretely distributed form can be a dot shape or an island shape, or a discontinuous filmy form in which a discrete island form is connected partly. These forms can also be considered as one form of a discontinuous film. In the case where ice has a continuous filmy form, the ice can have a form in which the film thickness is uniform, or a form of a non-uniform film having a non-uniform film thickness. In the case where the ice is considered to have a filmy form, the average film thickness of the ice can be obtained by conversion from the mass, using the density of ice. In the case where the density of ice is defined to be 0.93 g/cm$^3$, the average ice amount of 10 ng/mm$^2$ corresponds to the average film thickness of 11 nm.

The ice 20 to be formed by the above-mentioned method is controlled to have such an attached amount and form that allow the primary beam 21 to reach the surface of the sample 19 and do not hinder the desorption of a constituent of the sample 19.

When ions are used for the primary beam, it is preferred that the amount of the ice 20 be 20 ng per mm$^2$ of the sample surface (20 ng/mm$^2$) or less, or in a range of 0.1 ng/mm$^2$ or more and 20 ng/mm$^2$ or less. Alternatively, it can also be considered that the appropriate average film thickness of the ice is 22 nm or less or in a range of 0.11 nm or more and 21.5 nm or less.

The inventors of the present invention have also found that the attached amount of the ice in which the attachment of water, a matrix, an alkali metal salt, or an acidic substance sufficiently exhibits the effect of enhancing an ionization efficiency is 10 nm/mm$^2$ or less, or in a range of 0.1 ng/mm$^2$ or more and 10 ng/mm$^2$ or less. This also means that the appropriate average film thickness of the ice is 11 nm or less or in a range of 0.1 nm or more and 11 nm or less, and it is preferred that the amount of the ice on the surface of the sample be controlled in these ranges.

Laser light can pass through ice in a greater amount compared with an ion beam and can ionize a wider region of a sample. According to the MALDI method, in general, a sample containing a matrix is used, and a laser having a pulse width of about several ns is used. A laser with which a sample is irradiated reaches a region of several μm in a depth direction of the sample. Then, the laser energy absorbed by the sample is converted into heat energy, and a part of the sample is gasified or sublimated and detected in an ionized form. Thus, when laser light is used for the primary beam, it is preferred that the amount of the ice 20 be 1,000 ng/mm$^2$ or less, or in a range of 0.1 ng/mm$^2$ or more and 1,000 ng/mm$^2$ or less. Alternatively, it can also be considered that the appropriate average film thickness of the ice is 1,075 nm or less or in a range of 0.1 nm or more and 1,075 nm or less.

As an example of a method of controlling the amount of the ice to be formed on the surface of the sample 19, there is a method of measuring an attached amount of ice by using a reflectance change of infrared light or visible light and controlling the attached amount of ice so that an appropriate amount of ice is formed. Further, as an example of the method, there is a method of providing a crystal oscillator sensor (Quartz Crystal Microbalance (QCM)) in the vicinity of the sample 19 and keeping the sensor at the same temperature as that of the sample, measuring the mass of ice to be attached to the sample, and controlling the mass of the ice to be attached to the sample so that an appropriate amount of ice is formed. Alternatively, as an example of the method, there is a method of calculating an incident flux of water molecules impacting onto the sample from the partial pressure and introduction time of water to be introduced and the sample temperature to calculate an attached amount of ice, and controlling the attached amount of ice so that an appropriate amount of ice is formed.

Note that, an optimum amount of the ice 20 varies depending upon the configuration of a mass spectroscope to be used and the kind of a sample. As an example of a unit for obtaining the amount of ice optimum for the configuration of a mass spectroscope to be used and the kind of a sample, there is a method of preparing a sample with an excess amount of ice temporarily formed thereon previously, and reducing the attached amount of the ice 20 gradually by raising the temperature of a substrate while measuring the sample in the measurement chamber 11. The ion signal intensities of water molecule ions ($H_3O^+$) and sample constituent ions obtained from several samples 19 obtained by changing the amount of the ice 20 are measured by mass spectrometry to create a signal intensity correlation table of the $H_3O^+$ ions and the sample constituent ions. From the correlation table, the value of a signal intensity of $H_3O^+$ corresponding to the preferred attached amount of the ice 20 can be obtained. Further, several samples 19 obtained by changing the attached amount of the ice 20 are subjected to mass spectrometry, regarding a substrate portion on the side of the sample 19 in which the sample is not placed, and a signal intensity correlation table of the $H_3O^+$ ions and the sample constituent ions is created. The signal intensity of $H_3O^+$ obtained from the substrate portion on the side of the sample 19 does not contain a signal of water contained in the sample 19. Therefore, a value of the signal intensity of $H_3O^+$ corresponding to the preferred attached amount of the ice 20 can be obtained more precisely from the correlation table.

After creating the above-mentioned correlation table, when mass analysis of the sample 19 of the same kind is performed with the same analyzer configuration, the amount of the ice 20 is regulated so that the signal intensity of $H_3O^+$ takes an optimum value, with reference to the correlation table. Specifically, when the amount of the ice 20 is large, the ice 20 is reduced by raising the substrate temperature, and when the amount of the ice 20 is small, the above-mentioned step of forming ice is repeated. By measuring the constituent of the sample 19 after regulating the ice 20 to an optimum amount, the measurement with high reproduction precision can be repeated in an optimum state.

Further, in a long-term measurement, the attached amount of the ice 20 can be checked, if required, by measuring the substrate portion on the side of the sample 19. When the amount of the ice 20 is large, the ice 20 is reduced by raising the substrate temperature. When the amount of the ice 20 is small, the ice 20 is increased by repeating the above-mentioned step of forming ice. Thus, the measurement can be performed with the sample constantly holding an optimum amount of ice 20. Further, the attached amount of the ice 20 can be kept constant for a long period of time by keeping the sample temperature at a vaporization temperature of the ice or lower and in such a temperature and vacuum condition that the attachment of water molecules remaining in a vacuum can be suppressed.

Figure 2:
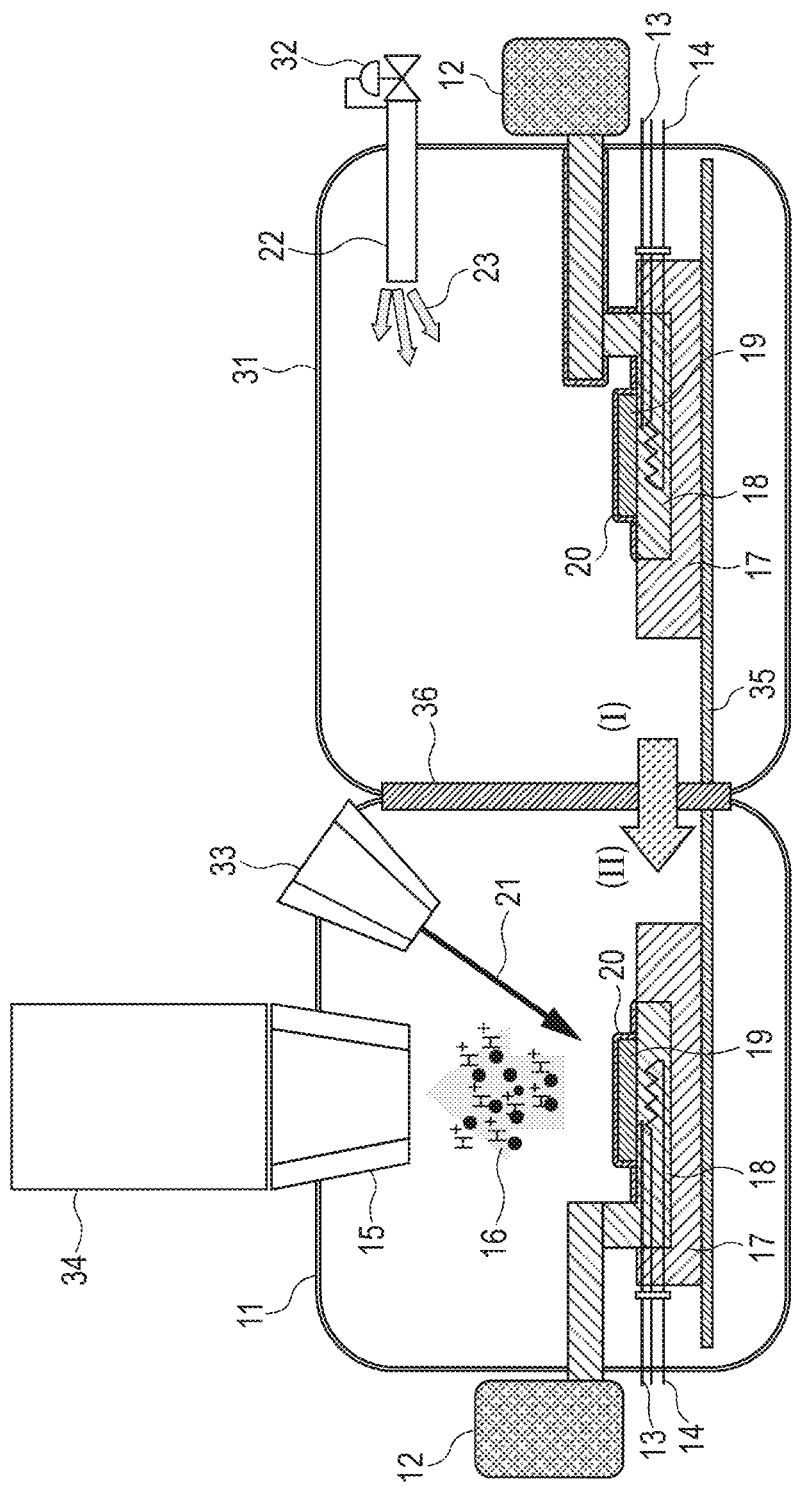
FIG. 2 is a schematic view of the analyzer used in Examples 1 to 3.

FIG. 1 illustrates a configuration in which the above-mentioned step of forming an ice layer and the step of irradiating the surface of the sample with the primary beam are performed in the same measurement chamber 11, but the present invention is not limited thereto, and a chamber to be used in the step of forming an ice layer and a chamber to be used in the step of irradiating the surface of the sample with the primary beam may be separated from each other as illustrated in FIG. 2. In this case, a movement mechanism 35 that moves the sample in a cooled state may be provided. Further, an open/close mechanism 36 may be provided between the chambers so that discharged water does not enter the measurement chamber 11.

Mass Analysis of a Constituent

After the ice 20 is formed, the gas-liquid mixing valve 25 is closed to exhaust gas while the temperature of the sample 19 is kept, and then, mass analysis is performed. The protonation to a sample constituent is promoted by the action of the ice 20 formed on the surface, and the constituent of the sample 19 can be detected at high sensitivity. Further, by allowing a water-soluble component to be attached to the sample in an ice form, the outflow of the solution component of the sample 19 can be suppressed, and the constituent of the sample 19 can be detected with the original information on a distribution of the constituent of the sample 19 kept. Further, the attached amount of the ice 20 can be kept constant for a long period of time by keeping, even during mass analysis, the sample temperature at a vaporization temperature of the ice or lower and such a temperature and vacuum condition that the attachment of water molecules remaining in a vacuum can be suppressed, and the constituent can be detected stably for a long period of time.

EXAMPLES

Hereinafter, the present invention is described more specifically by way of examples and comparative examples. The following specific examples are those of the best embodiment according to the present invention, but the present invention is not limited to such specific embodiment.

Example 1

Effect 1 in TOF-SIMS Measurement

Preparation of a Sample

In Example 1, a peptide molecule derived from a human "Angiotensin II (Mw: 1046, produced by California Peptide Research Inc.)" was used as an object to be measured. First, a solution in which the object to be measured is dissolved in ion exchange water in $10^{-6}$ M was prepared. An inkjet print dot pattern of Angiotensin II was used, which was formed on a silicon wafer by an inkjet ejection unit (product name: Pulse injector, produced by Cluster technology Co.), using the solution. The size of one dot to be formed by printing is about 120 µm in diameter, and about 30 fmol of Angiotensin II molecules are present in each dot. The dot can be measured to be used for the comparison of detection intensities and the evaluation of the outflow of a constituent.

Formation of Ice Containing only Water

The mass spectroscope of the present invention to be used in the example has a two-chamber configuration formed of the measurement chamber 11 and a pre-chamber 31, as illustrated in FIG. 2, each of which has a mechanism through which a sample holder 17 can move. First, ice 20 containing only water was formed on a sample in the pre-chamber 31 ((I) of FIG. 2).

A dot pattern sample 19 of Angiotensin II was fixed onto the sample holder 17, and the sample holder 17 was set in the pre-chamber 31. Then, the pre-chamber 31 was exhausted to a vacuum of $2 \times 10^{-6}$ Pa. After that, the sample 19 was cooled to $-140°$ C., and an $H_2O$ leaking valve 32 was opened. As the pre-chamber 31 was being filled with gas containing water, the ice 20 was formed on the surface of the sample 19. At that time, the attached amount of the ice was obtained by using the crystal oscillator sensor, and a predetermined amount of the ice was allowed to be attached onto the sample 19. After that, the $H_2O$ leaking valve 32 was closed. The introduced gas was discharged with the temperature of the sample 19 kept at about $-140°$ C., and then the sample 19 was moved together with the sample holder 17 into the measurement chamber 11. Then, a mass analysis of the sample 19 was performed ((II) of FIG. 2).

TOF-SIMS Measurement

As the mass spectrometry, a TOF-SIMS measurement method was used. The measurement was performed under the following measurement condition, using a TOF-SIMS 5 apparatus (trade name) produced by ION-TOF Co.

Primary ions: 25 kV $Bi^{3+}$, 1 pA (pulse current value), random scan mode
Pulse frequency of primary ions: 5 kHz (200 µs/shot)
Pulse width of primary ions: about 1 nanosecond
Primary ion beam diameter: about 1 µm
Measurement area: 200 µm×200 µm
Measurement point number of secondary ions: 128×128 points
Accumulated time: 16 scans (about 52 seconds)
Secondary ion extraction electrode voltage: −2 kV
Detection mode of secondary ions: positive ions The measurement was performed for each one dot of the dot pattern of Angiotensin II.

Increase in a Detection Intensity by the Formation of Ice

Figure 3A:
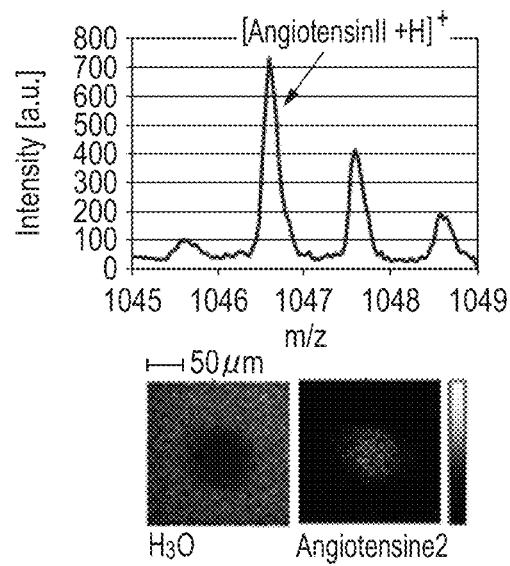
FIGS. 3A, 3B, 3C, 3D and 3E show TOF-SIMS mass spectra and ion images thereof obtained in Example 1 and Comparative Examples 1-1 to 1-4.

After ice was attached to the surface of the sample in an amount of about 1 ng per $mm^2$ by the above-mentioned method, a mass spectrum of [Angiotensin II+H]$^+$ (m/z: 1046.8) was detected from one dot of Angiotensin II measured at a sample temperature of $-140°$ C. FIG. 3A shows the mass spectrum. FIG. 3A also shows, in a lower part, the respective ion images of water molecule ions [$H_3O$]$^+$ (m/z: 19) and [Angiotensin II+H]$^+$, obtained simultaneously. The amount of applied ice of 1 ng/$mm^2$, when converted into an average film thickness assuming that the density of ice was about 0.93 g/$cm^3$, was calculated to be about 1.1 nm.

Comparative Example 1-1

Figure 3B:
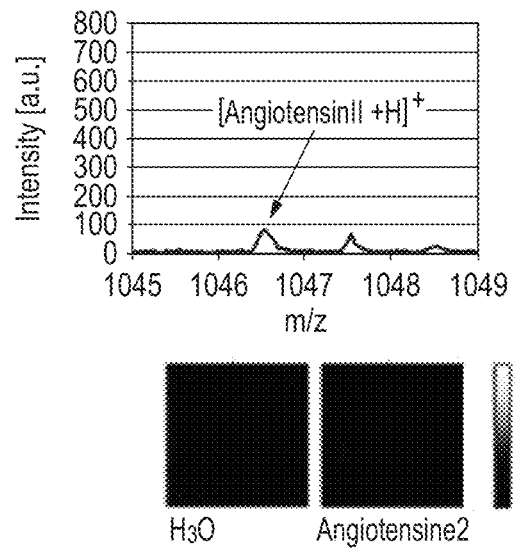

As a comparison, one dot of the same Angiotensin II with no ice attached thereto was measured at a sample temperature of 25° C. FIG. 3B shows a mass spectrum of [Angiotensin II+H]$^+$. FIG. 3B also shows, in a lower part, ion images of [$H_3O$]$^+$ and [Angiotensin II+H]$^+$, obtained simultaneously.

Here, FIGS. 3A to 3E illustrate, on the same display scale, both spectrum intensities and image intensities.

In the sample produced in Example 1, ice is applied, and hence the signal intensity of $[H_3O]^+$ is high (FIG. 3A). On the other hand, in the sample of FIG. 3B, ice is not applied, and hence the signal intensity of $[H_3O]^+$ is low. In the mass spectrometry measurement of the sample provided with ice in this method, compared with the measurement of the sample not provided with ice, the ion detection intensity of [Angiotensin II+H]$^+$ that is a sample constituent is about 9 times. This is considered to be caused by the fact that the efficiency of protonation to the sample constituent varies depending upon the difference in the attached amount of ice.

Comparative Example 1-2

Figure 3C:
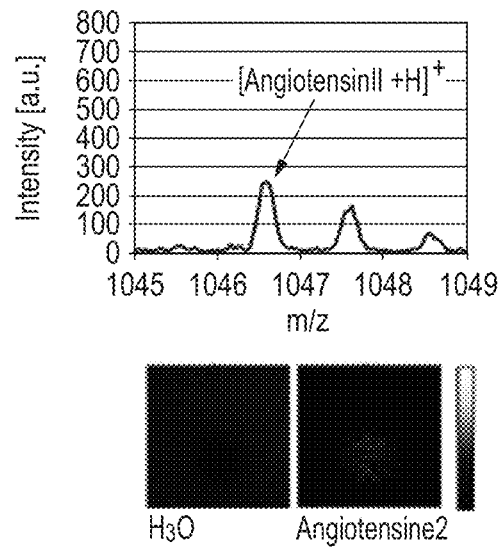

As a comparison, one dot of Angiotensin II cooled to a sample temperature of −140° C. was measured. FIG. 3C shows a mass spectrum of [Angiotensin II+H]$^+$. FIG. 3C also shows, in a lower part, ion images of $[H_3O]^+$ and [Angiotensin II+H]$^+$, obtained simultaneously.

Compared with the sample not provided with ice (FIG. 3B), the signal intensity of $[H_3O]^+$ of FIG. 3C is high. However, compared with the sample provided with ice by the method of Example 1 (FIG. 3A), the signal intensity of $[H_3O]^+$ of FIG. 3C is low. Further, the detection intensity of [Angiotensin II+H]$^+$ that is the sample constituent of FIG. 3C is lower than that of FIG. 3A and is higher than that of FIG. 3B. The reason for this is considered as follows. A small amount of water molecules remaining in the measurement chamber are attached to a sample by cooling, and hence the efficiency of protonation to the sample constituent is higher than that of the sample not provided with ice (FIG. 3B). However, an appropriate amount of ice is not applied, and hence the efficiency of protonation to the sample constituent is lower than that of the sample provided with ice by the method of Example 1 (FIG. 3A). In this comparative example, the attached amount of water is estimated from an incident flux of water molecules impacting onto the sample to be about 0.1 ng/mm$^2$.

Comparative Example 1-3

Figure 3D:
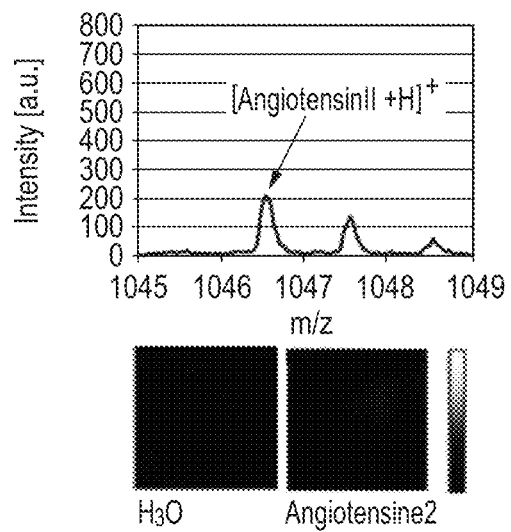

As a comparison, a dot pattern sample of Angiotensin II cooled to a sample temperature of −140° C. in the pre-chamber 31 in a vacuum was left in the atmosphere (humidity: 20%) for three minutes to produce a sample to which water in the atmosphere was attached in an ice form. The inside of the chamber was again exhausted to a vacuum without cooling the sample. FIG. 3D shows a mass spectrum of [Angiotensin II+H]$^+$ detected under the above-mentioned measurement condition without cooling and ion images of $[H_3O]^+$ and [Angiotensin II+H]$^+$.

Compared with the sample provided with ice by the method of Example 1 (FIG. 3A), the detection intensity of [Angiotensin II+H]$^+$ that is the sample constituent is lower in the sample of FIG. 3D. The reason for this is assumed as follows. As is understood from the fact that the signal intensity of $[H_3O]^+$ of FIG. 3D is low, water in the atmosphere adsorbs to the cooled sample by leaving the sample in the atmosphere, but the sample temperature increases when the sample is returned to the vacuum without being cooled, and thus the water component adsorbing to the sample vaporizes rapidly. As a result, the attached water amount is reduced, and the protonation to the sample constituent is not promoted sufficiently. Hence, the detection intensity of [Angiotensin II+H]$^+$ that is the sample constituent becomes low.

Comparative Example 1-4

Figure 3E:
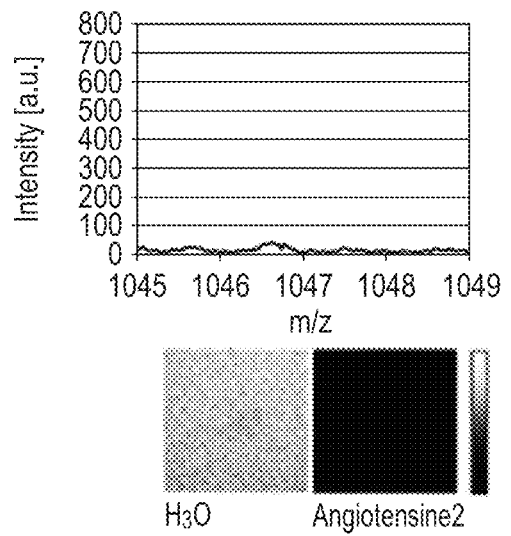

As in Comparative Example 1-3, a dot pattern sample of Angiotensin II cooled to a sample temperature of −140° C. in the pre-chamber 31 under a vacuum was left in the atmosphere (humidity: 20%) for three minutes to produce a sample to which water in the atmosphere was attached in an ice form. The inside of the chamber was again exhausted to a vacuum while cooling the sample to a sample temperature of −140° C. FIG. 3E shows a mass spectrum of [Angiotensin II+H]$^+$ detected under the same measurement condition described above while being cooled and ion images of $[H_3O]^+$ and [Angiotensin II+H]$^+$.

Compared with the sample provided with ice by the method of Example 1 (FIG. 3A), the detection intensity of [Angiotensin II+H]$^+$ that is the sample constituent is lower in the sample of FIG. 3E. The reason for this is considered as follows. As is understood from the fact that the signal intensity of $[H_3O]^+$ of FIG. 3E is high, a large amount of ice 20 is formed on the surface of the sample. Therefore, the ions of the primary beam 21 cannot reach the surface of the sample sufficiently or the desorption of the sample constituent ions is inhibited, with the result that the detection intensity of [Angiotensin II+H]$^+$ that is the sample constituent decreases. Thus, it can be understood that, according to the method of allowing water in the atmosphere to adsorb to the cooled sample by leaving the sample in the atmosphere, and performing the measurement while the sample remains cooled, the ice is formed in an excess amount and the detection intensity of the sample constituent becomes low.

Change in a Detection Intensity of a Constituent According to an Attached Amount of Ice In order to examine change in the detection intensity of the constituent of the sample 19 with respect to the attached amount of the ice 20 to be formed, there were prepared dot pattern samples of the above-mentioned Example 1, Comparative Examples 1-1 to 1-4, and of Angiotensin II in which the attached amount of the ice 20 was varied. One dot of each of the samples was subjected to mass analysis under the same condition as described above, and FIG. 4A shows a relationship in peak area intensity between [Angiotensin II+H]$^+$ and $[H_3O]^+$ in the obtained mass spectrum. Respective data points 41, 42-1, 42-2, 42-3, and 42-4 indicated by indices in the graph represent values obtained in Example 1 and Comparative Examples 1-1, 1-2, 1-3, and 1-4. Further, FIG. 4B shows a relationship between the attached amount of the ice of each sample measured by using the crystal oscillator sensor and the peak area intensity of [Angiotensin II+H]$^+$.

Figure 4A:
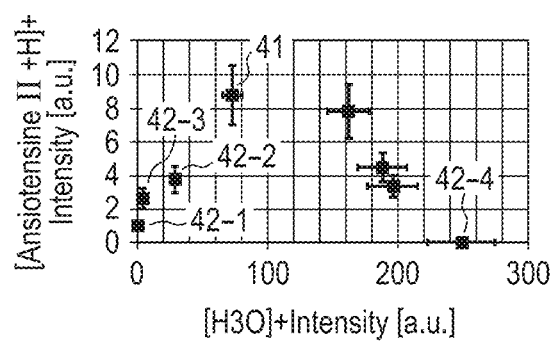
FIG. 4A shows a relationship in a peak area intensity between a water molecule ion and a constituent ion in Example 1 and Comparative Examples 1-1 to 1-4.
Figure 4B:
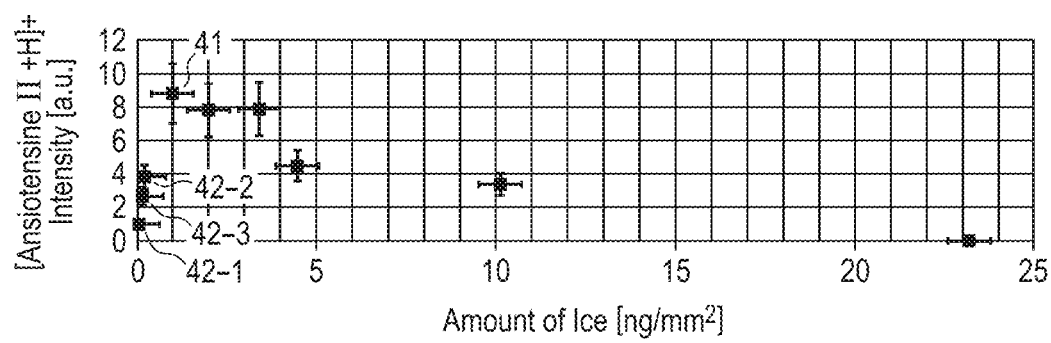
FIG. 4B shows a relationship between a peak area intensity of a constituent ion and an amount of provided ice.

In FIG. 4A, the peak area intensity of $[H_3O]^+$ on the horizontal axis correlates with the attached amount of the ice 20 to be formed. As is understood from the graph of FIG. 4A, the detection intensity of the constituent of the sample 19 changes by varying the attached amount of the ice 20.

Further, as described in Comparative Example 1-4, a great amount of the ice 20 is formed on the surface of the sample at the data point indicated by the index 42-4, and hence the primary beam 21 cannot pass through the ice 20 sufficiently. As a result, the detection intensity of the constituent of the sample is decreased. In the vicinity of the positions of the peak area intensity of $[H_3O]^+$ of the horizontal axis, which are indicated by the indices 42-1, 42-2, and 42-3, the ice is not formed in an amount capable of sufficiently promoting the protonation to the sample constituent. On the other hand, it is shown that, in the vicinity of the position of the peak area intensity of $[H_3O]^+$ of the horizontal axis, which is indicated by the index 41, the ice is held in an amount capable of sufficiently promoting the protonation to the sample constituent. It is understood from FIG. 4B that, if the amount of the ice to be attached is 20 ng per mm$^2$ (20 ng/mm$^2$) or less of the surface of the sample, the protonation to the sample constituent can be promoted.

It is understood from the above that, in order to increase the detection intensity of the constituent of the sample 19 and measure the detection intensity stably, it is necessary to form the ice 20 in an appropriate amount on the surface of the sample, and keep that state constant. In order to keep the state of the ice 20 thus formed constant, it is effective to keep the temperature of the sample 19 at the vaporization temperature of the ice and keep the temperature and vacuum condition capable of preventing the attachment of water molecules remaining in a vacuum.

Figure 4C:
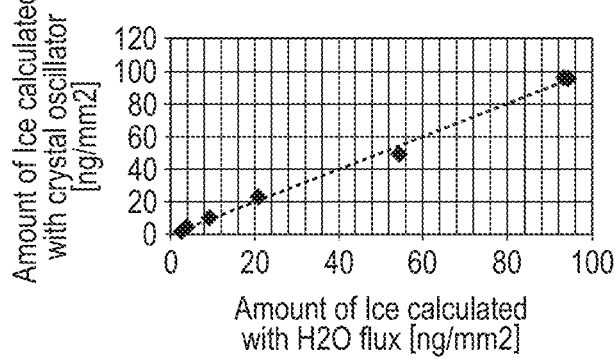
FIG. 4C shows a relationship between an amount of provided ice measured from an incident flux of water molecules and an amount of provided ice measured by using a crystal oscillator monitor.

FIG. 4C shows, in the step of attaching the ice, results of the comparison between the attached amount of the ice calculated from the incident flux of water molecules impacting onto the sample and the attached amount of the ice measured by using the crystal oscillator monitor. The incident flux of water molecules is obtained by measuring the water partial pressure in the pre-chamber 31, using a quadrupole mass spectroscope, according to the kinetic theory of gas molecules. The results obtained by both methods are proportional, and the attached amount of the ice can be obtained with good precision using any of the measurement methods.

Holding information on a distribution of a sample constituent by the formation of ice First, before forming the ice, a dot pattern sample of Angiotensin II was measured in the measurement chamber 11 in advance under the above-mentioned measurement condition. Then, the sample was moved to the pre-chamber 31, and the ice was formed on the surface of the sample by the above-mentioned method. After that, the sample was returned to the measurement chamber 11 again, and the dot in the same portion as that described above was measured under the same measurement condition. FIG. 5A shows the ion images of water molecule ions $[H_3O]^+$ (m/z: 19), sodium ions $[Na]^+$ (m/z: 23), and $[Angiotensin\ II+H]^+$ (m/z: 1046.8), detected from one dot of Angiotensin II before the formation of the ice. FIG. 5B shows ion images of the same kinds as those of FIG. 5A measured from the dot in the same portion as that of FIG. 5A after the formation of the ice. Here, sodium is contained previously in the sample as impurities. As is understood from FIGS. 5A and 5B, a component of an object does not flow out even after the formation of the ice, and the original information on a distribution thereof is held.

Comparative Example 1-5

An example of comparing the holding states of the information on a distribution of the sample constituent is described. FIG. 5C shows ion images of the same kinds as those of FIGS. 5A and 5B in the case of dropping water liquid droplets (2 μl) onto a dot pattern sample of Angiotensin II with a micropipetter in the atmosphere at room temperature and performing measurement under the same measurement condition as described above. In FIG. 5C, the ion images of $[Na]^+$ and $[Angiotensin\ II+H]^+$ are spread to the entire surface. This is because the sample constituent flows out into the liquid droplets due to the application of the solution by dropping the liquid droplets. Thus, it can be understood that, with the provision of the solution by dropping the liquid droplets, the original information on a distribution of the sample constituent is not held.

Comparative Example 1-6

An example of comparing the holding states of the information on a distribution of the sample constituent is described. In the same way as in Comparative Example 1-2, a dot pattern sample of Angiotensin II, in which the sample temperature was cooled to −140° C. in the pre-chamber 31 under a vacuum, was left in the atmosphere (humidity: 20%) for three minutes, to thereby produce a sample to which water in the atmosphere was attached in an ice form. The chamber was vacuumized again without cooling the sample, and FIG. 5D shows ion images of the same kinds as those of FIGS. 5A to 5C, detected under the same measurement condition as described above without cooling the sample. In FIG. 5D, the ion images of $[Na]^+$ and $[Angiotensin\ II+H]^+$ are spread and the contour thereof is unclear. The reason for this is as follows. Water in the atmosphere adsorbs to the cooled sample when the sample is placed in the atmosphere, but the ice component adsorbing to the sample dissolves on the surface of the sample during the process of returning the sample into the vacuum without cooling. As a result, a water-soluble sample constituent flows out thereonto. Thus, it is understood that, according to the method of performing the measurement without cooling the sample provided with the ice formed in the atmosphere, the original information on a distribution of the sample constituent is not held.

Example 2

Effect 2 in TOF-SIMS Measurement

Preparation of a Sample

In Example 2, a peptide molecule derived from a bovine, "Insulin: hereinafter, referred to as "insulin" (Mw: 5733.8, SIGMA CHEMICAL CO.)", is used as an object to be measured. First, a solution in which the object to be measured is dissolved in ion exchange water in $10^{-7}$M is prepared. An inkjet print dot pattern of insulin is formed on a gold-deposition/silicon wafer substrate by an inkjet ejection unit in the same way as in Example 1, using the solution. At this time, the size of one dot to be formed by printing is about 120 μm in diameter, and about 40 fmol of insulin molecules are present in each dot.

Further, in Example 2, in the TOF-SIMS measurement, an aqueous solution of trifluoroacetic acid (hereinafter, referred to as TFA, produced by SIGMA CHEMICAL CO.) of an acidic substance for further promoting the protonation to a sample constituent is provided. An aqueous solution containing 0.1 wt % of TFA is produced.

Formation of Ice Containing an Acidic Substance

Ice containing TFA is formed. The TFA aqueous solution is mixed with nitrogen gas that is carrier gas, and the leaking valve 32 is opened so that the nitrogen gas containing about 5% of the TFA aqueous solution is discharged through the leaking nozzle 22 and sprayed onto the surface of the sample. After a predetermined amount of the TFA aqueous solution is sprayed, the leaking valve 32 is closed, and the pre-chamber 31 is returned to a vacuum again. Then, the sample 19 is moved together with the sample holder 17 into the measurement chamber 11 with the temperature of the sample 19 kept low, and the mass analysis of the sample 19 is performed.

TOF-SIMS Measurement

As the mass spectrometry, a TOF-SIMS measurement method is used. The measurement is performed under the same measurement condition as in Example 1.

Figure 6A:
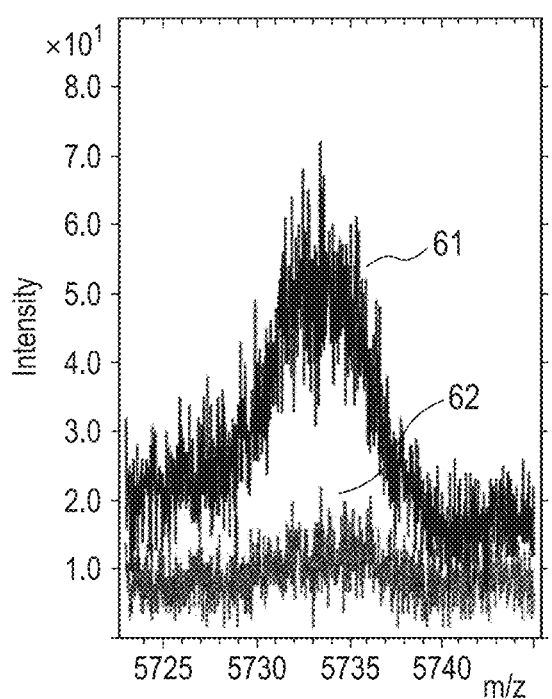
FIGS. 6A and 6B show TOF-SIMS mass spectra and ion images thereof obtained in Example 2 and Comparative Example 2.
Figure 6B:
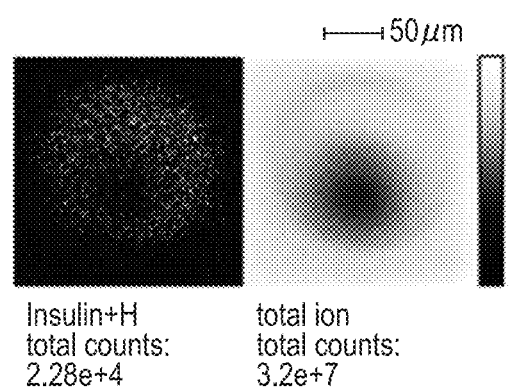

Increase in Detection Intensity by the Formation of Ice Containing an Acidic Substance FIG. 6A shows a mass spectrum 61 of $[Insulin+H]^+$ (m/z: 5734.6) detected from one dot of insulin after the formation of ice containing the TFA component, using the above-mentioned method, and FIG. 6B shows ion images of [Insulin+H]$^+$ and total ions obtained by the same measurement.

Comparative Example 2

As a comparison, FIG. 6A also shows a mass spectrum 62 of [Insulin+H]$^+$ in the case of producing an insulin dot previously containing a TFA component by the same method as described above, using an aqueous solution mixed with 0.1 wt % of TFA, and detecting the mass spectrum under the same measurement condition without forming ice.

As is understood from the spectra 61 and 62 of FIG. 6A, a constituent of the object is detected strongly from an insulin dot provided with a TFA component as ice, even in the same insulin dot containing the TFA component. The reason for this is assumed as follows. A water component is held on the sample due to the formation of ice to promote the protonation to a sample constituent by the action of an acidic substance, and the ionization efficiency is further enhanced.

Further, as is understood from FIG. 6B, due to the formation of ice containing the TFA component, a sample constituent can be detected while preventing the outflow of the sample constituent.

Example 3

Effect in MALDI Measurement

Preparation of a Sample

In Example 3, a peptide molecule derived from a bovine, "Insulin Chain-B, Oxidized (hereinafter, referred to as "InsB", Mw: 3495.9, SIGMA CHEMICAL CO.)", is used as an object to be measured. First, a solution in which the object to be measured is dissolved in ion exchange water in $10^{-7}$M is prepared. An inkjet print dot pattern of InsB is formed on a MALDI sample holder made of stainless steel by an inkjet ejection unit in the same way as in Example 1, using the solution. At this time, the size of one dot to be formed by printing is about 140 μm in diameter, and about 40 fmol of InsB molecules are present in each dot.

Further, in Example 3, in the MALDI measurement, an aqueous solution of 2,5-dihydroxybenzoic acid (DHBA, produced by BRUKER DALTONICS Co.), which is a matrix agent for further promoting the protonation to a sample constituent, is provided. An aqueous matrix solution is prepared by dissolving 10 mg/mL of the DHBA in a solution (acetonitrile:water=1:1 (volume ratio)).

Formation of Ice Containing a Matrix

Ice containing the matrix is formed by the same method as that of Example 2. The matrix aqueous solution is mixed with nitrogen gas that is carrier gas, and the leaking valve 32 is opened so that the nitrogen gas containing about 5% of the matrix aqueous solution is discharged through the leaking nozzle 22 and sprayed onto the surface of a sample. After a predetermined amount of the nitrogen gas is sprayed, the leaking valve 32 is closed, and the pre-chamber 31 is returned to a vacuum again. Then, the sample 19 is moved together with the sample holder 17 into the measurement chamber 11 with the temperature of the sample 19 kept lower, and the mass analysis of the sample 19 is performed.

MALDI Measurement

A MALDI method is used as mass spectrometry. The measurement chamber 11 of FIG. 2 is an apparatus in which a sample cooling mechanism is provided to autoflex speed (trade name) produced by BRUKER DALTONICS Co. The measurement condition is as follows.

Primary laser pulse beam: wavelength 337 nm, output 20%
Pulse frequency of laser: 10 Hz
Pulse width of primary ions: about 3 nanoseconds
Primary ion beam diameter: about 5 μm
Accumulated time: 10 scans
Secondary ion extraction electrode voltage: −2 kV
Detection mode of secondary ions: positive ions, spectrum measurement
Sample temperature: −100° C.

Increase in Detection Intensity by the Formation of Ice Containing a Matrix

Figure 7:
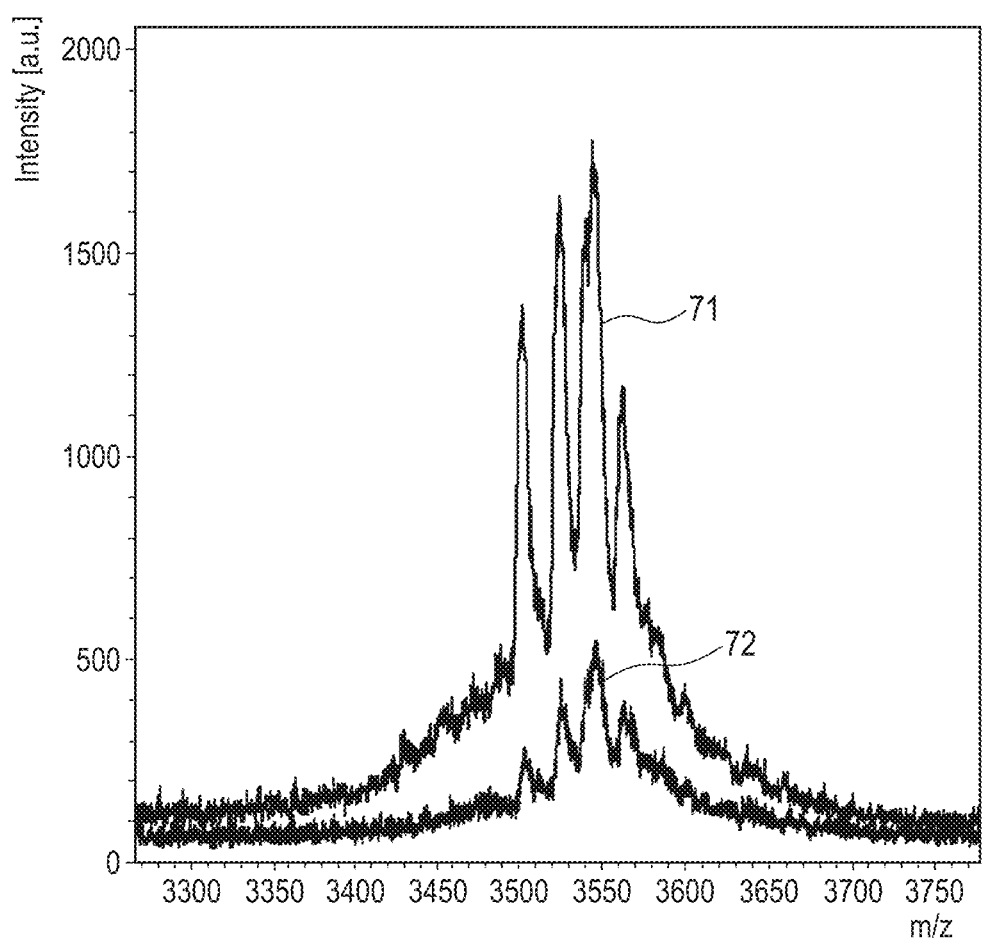
FIG. 7 shows MALDI mass spectra obtained in Example 3 and Comparative Example 3.

FIG. 7 shows a MALDI mass spectrum 71 of [InsB+H]$^+$ detected under the above-mentioned measurement condition from one dot of InsB after the formation of ice containing the matrix.

Comparative Example 3

As a comparison, an aqueous solution in which the matrix solution and the InsB solution are mixed in a ratio of 1:1 is produced, and an InsB dot previously containing the matrix component is produced by the same method as described above. FIG. 7 also shows a MALDI mass spectrum 72 of [InsB+H]$^+$ in the case of detecting the insB dot under the same measurement condition without forming ice.

As is understood from the spectra 71 and 72 of FIG. 7, a constituent of the object is strongly detected from a sample of the InsB dot provided with the matrix component as ice, in the InsB dot containing the matrix component. The reason for this is assumed as follows. A water component is held on the sample due to the formation of ice to promote the protonation to a sample constituent by the action of the matrix, and an ionization efficiency is further enhanced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2011-006094, filed Jan. 14, 2011, and 2011-251621, filed Nov. 17, 2011, which are hereby incorporated by reference herein in their entirety.

REFERENCE SIGNS LIST

11: measurement chamber
12: liquid nitrogen tank
13: thermocouple
14: heating wire heater
15: extraction electrode
16: sample component ion
17: sample holder
18: sample cooling mechanism
19: sample
20: ice
21: primary beam
22: gas leaking nozzle
23: gas containing solution
24: solution tank
25: gas-liquid mixing valve
26: carrier gas cylinder
31: pre-chamber
32: leaking valve
41: peak area intensity of [Angiotensin II+H]$^+$ obtained in Example 1

42-1: peak area intensity of [Angiotensin II+H]⁺ obtained in Comparative Example 1-1
42-2: peak area intensity of [Angiotensin II+H]⁺ obtained in Comparative Example 1-2
42-3: peak area intensity of [Angiotensin II+H]⁺ obtained in Comparative Example 1-3
42-4: peak area intensity of [Angiotensin II+H]⁺ obtained in Comparative Example 1-4
61: TOF-SIMS mass spectrum obtained in Example 2
62: TOF-SIMS mass spectrum obtained in Comparative Example 2
71: MALDI mass spectrum obtained in Example 3
72: MALDI mass spectrum obtained in Comparative Example 3

The invention claimed is:

1. A sample analysis method comprising the steps of:
cooling a sample placed in a chamber;
forming an ice layer on a surface of the cooled sample by discharging one of water and an aqueous solution to the chamber;
irradiating the surface of the sample with a primary ion beam through the ice layer so as to emit a sample constituent from the sample under the ice layer as a secondary ion; and
analyzing the secondary ion emitted from the sample under the ice layer due to the irradiation,
wherein the sample constituent is protonated,
wherein protonation of the sample constituent is promoted by the ice layer, and
wherein an amount of water forming the ice layer is from 0.1 ng/mm² to 20 ng/mm².

2. The method according to claim 1, wherein the cooling step is performed in a depressurized chamber.

3. The method according to claim 1, wherein the step of forming the ice layer comprises controlling an amount of ice to be formed by using at least one of methods (1) to (4):
(1) a method using a reflectance change of one of infrared light and visible light;
(2) a method using a crystal oscillator sensor;
(3) a method using a measured value of a water partial pressure; and
(4) a method using a signal intensity correlation table in mass analysis of a water molecule ion and a sample constituent ion.

4. The method according to claim 1, wherein the aqueous solution is discharged in the step of forming the ice layer, and wherein a solute component of the aqueous solution comprises one substance selected from the group consisting of a matrix, an alkali metal salt, and an acidic substance.

5. The method according to claim 1, wherein a component of the sample comprises at least one selected from the group consisting of a protein, a peptide, a sugar chain, a polynucleotide, and an oligonucleotide.

6. An analyzer of irradiating a sample with a primary beam to analyze an ion emitted from the sample, the analyzer comprising:
a chamber in which a sample is to be placed;
a primary beam generating unit for irradiating a surface of the sample in the chamber with the primary beam;
a cooling mechanism for cooling the sample in the chamber;
a nozzle for discharging one of water and an aqueous solution to the chamber;
an extraction electrode for guiding a secondary ion emitted from the sample to a mass analysis unit; and
a control unit for controlling an amount of the one of the water and the aqueous solution to be discharged from the discharge unit to the chamber,
wherein one of the water and the aqueous solution is discharged from the discharge unit with the sample placed in the chamber being cooled to form an ice layer on the surface of the sample,
wherein the control unit controls an amount of water forming the ice layer to be from 0.1 ng/mm² to 20 ng/mm²,
wherein irradiation of the primary beam ionizes the sample to be analyzed through the ice layer,
wherein a sample constituent is emitted from the sample under the ice layer as the secondary ion before reaching the mass analysis unit,
wherein the sample constituent is protonated, and
wherein protonation of the sample constituent is promoted by the ice layer.

7. The analyzer according to claim 6, wherein the primary beam is an ion beam.

8. The analyzer according to claim 6, further comprising at least one of units (1) to (4) for measuring the ice layer:
(1) a detection unit for one of infrared light and visible light for measuring a reflectance change;
(2) a crystal oscillator sensor;
(3) a measurement unit for a water partial pressure; and
(4) a unit for obtaining signal intensity correlation information in mass analysis of a water molecule ion and a sample constituent ion.

9. The analyzer according to claim 6, wherein the extraction electrode is arranged so as to oppose the surface of the sample.

10. The analyzer according to claim 9, wherein the extraction electrode is arranged vertically above the sample.

11. The analyzer according to claim 10, wherein the nozzle is arranged at a position higher than the sample and lower than the extraction electrode.

12. The analyzer according to claim 6, wherein the nozzle and the extraction electrode are separated from each other by an open/close mechanism.

13. The analyzer according to claim 6, further comprising a mount portion for mounting the sample thereon.

14. The analyzer according to claim 13, wherein a tank for cooling the mount portion by thermal contact is provided outside the chamber.

15. The method according to claim 1, wherein the ice layer promotes protonation to the sample to promote ionization of the sample.

16. The method according to claim 1, wherein an ion of the sample to which hydrogen is added is analyzed.

17. The method according to claim 1, wherein the step of forming the ice layer comprises controlling an amount of ice to be formed by using a signal intensity correlation table in mass analysis of an $H_3O^+$ ion and a protonated sample constituent ion.

18. The method according to claim 1, wherein the mass spectrometry is performed while monitoring an amount of the ice layer.

19. The method according to claim 1, wherein the amount of the water forming the ice layer is controlled based on a result of the mass spectrometry.

20. The method according to claim 1, wherein the aqueous solution is discharged in the step of forming the ice layer, and wherein a solute component of the aqueous solution comprises a substance selected from the group consisting of an alkali metal salt and an acidic substance.

* * * * *